United States Patent
Isaacs

(10) Patent No.: US 11,793,950 B2
(45) Date of Patent: Oct. 24, 2023

(54) MEDICAMENT DELIVERY DEVICE AND METHOD

(71) Applicants: Propel-AIR BioPharma, LLC, Oceanside, NY (US); ACERUS BIOPHARMA INC., Mississauga (CA)

(72) Inventor: Ari Isaacs, Oceanside, NY (US)

(73) Assignees: PROPEL-AIR BIOPHARMA, LLC, Oceanside, NY (US); ACERUS BIOPHARMA INC., Mississauga (CA)

( * ) Notice: Subject to any disclaimer, the term of this patent is extended or adjusted under 35 U.S.C. 154(b) by 0 days.

(21) Appl. No.: 16/071,648

(22) PCT Filed: Feb. 6, 2017

(86) PCT No.: PCT/US2017/016706
§ 371 (c)(1),
(2) Date: Jul. 20, 2018

(87) PCT Pub. No.: WO2017/136825
PCT Pub. Date: Aug. 10, 2017

(65) Prior Publication Data
US 2019/0030266 A1  Jan. 31, 2019

Related U.S. Application Data

(60) Provisional application No. 62/404,878, filed on Oct. 6, 2016, provisional application No. 62/291,107, filed on Feb. 4, 2016.

(51) Int. Cl.
*A61M 15/00* (2006.01)
*A61M 15/08* (2006.01)
(Continued)

(52) U.S. Cl.
CPC ........ *A61M 15/0015* (2014.02); *A61J 7/0053* (2013.01); *A61M 11/02* (2013.01);
(Continued)

(58) Field of Classification Search
CPC .............. A61M 15/00; A61M 15/0001; A61M 15/0013; A61M 15/0015; A61M 15/0016;
(Continued)

(56) References Cited

U.S. PATENT DOCUMENTS 4,180,069 A * 12/1979 Walters ............. A61M 5/31515
604/228
4,263,868 A * 4/1981 Fukui .................... G01M 15/06
73/114.01
(Continued)

FOREIGN PATENT DOCUMENTS

GB 2391483 A 2/2005
GB 2440316 A 1/2008
(Continued)

OTHER PUBLICATIONS

Official Action dated Aug. 2, 2018, from Canadian Application No. 3,012,477.
(Continued)

*Primary Examiner* — Timothy A Stanis
*Assistant Examiner* — Matthew R Moon
(74) *Attorney, Agent, or Firm* — Katten Muchin Rosenman LLP

(57) ABSTRACT

A medicament delivery device is provided having an oral tubular section for placement in the mouth of a user and a nasal tubular section for placement in the naris of a user. A medicament located in a corrugated, or flexible, section joining the oral tubular section and the nasal tubular section is dispersed into the nasal cavity of the user by blowing into the oral tubular section. A pinch valve or a one way valve is used to prevent the user from accidentally inhaling the medicament. The medicament delivery device may also be used as a pulmonary delivery device into the mouth of a user.

9 Claims, 11 Drawing Sheets

(51) Int. Cl.
*A61M 11/02* (2006.01)
*A61J 7/00* (2006.01)
*A61M 31/00* (2006.01)
A61M 25/02 (2006.01)
A61M 25/04 (2006.01)

(52) U.S. Cl.
CPC .... *A61M 15/0013* (2014.02); *A61M 15/0098* (2014.02); *A61M 15/08* (2013.01); *A61M 31/00* (2013.01); *A61M 15/0043* (2014.02); *A61M 25/04* (2013.01); *A61M 2025/0226* (2013.01); *A61M 2202/064* (2013.01); *A61M 2205/075* (2013.01)

(58) Field of Classification Search
CPC .......... A61M 15/0028; A61M 15/0091; A61M 15/0093; A61M 15/0098; A61M 15/08; A61M 15/085; A61M 31/00; A61M 2202/06; A61M 2202/064; A61J 7/0053; A61J 7/0076
See application file for complete search history.

(56) References Cited

U.S. PATENT DOCUMENTS

| | | | |
|---|---|---|---|
| 4,579,114 A * | 4/1986 | Gray | A61M 16/0048 128/203.11 |
| 5,562,918 A * | 10/1996 | Stimpson | A61M 15/0028 128/200.24 |
| 5,797,392 A | 8/1998 | Keldmann et al. | |
| 5,878,743 A * | 3/1999 | Zdrojkowski | A61M 16/208 128/204.23 |
| 5,927,557 A * | 7/1999 | Busick | B67D 3/04 222/554 |
| 6,491,940 B1 | 12/2002 | Levin | |
| 6,715,485 B1 | 4/2004 | Djupesland | |
| 6,811,543 B2 | 11/2004 | Keldmann et al. | |
| 7,661,425 B2 | 2/2010 | Keldmann et al. | |
| 7,784,460 B2 | 8/2010 | Djupesland et al. | |
| 7,975,690 B2 | 7/2011 | Djupesland | |
| 8,381,732 B2 * | 2/2013 | Daly | A61M 16/06 128/200.24 |
| 8,522,778 B2 | 9/2013 | Djupesland | |
| 8,555,877 B2 | 10/2013 | Djupesland | |
| 8,596,278 B2 | 12/2013 | Djupesland | |
| 8,707,950 B1 | 4/2014 | Rubin | |
| 8,827,946 B2 * | 9/2014 | Tsutsui | A61K 9/0043 604/212 |
| 9,078,989 B2 * | 7/2015 | Genger | A61M 16/0666 |
| 9,114,204 B2 * | 8/2015 | Jeppson | A61M 3/0262 |
| 9,119,932 B2 | 9/2015 | Djupesland | |
| 9,440,039 B2 * | 9/2016 | Payton | A61M 16/0672 |
| 9,468,727 B2 | 10/2016 | Djupesland | |
| 9,566,397 B2 * | 2/2017 | Faram | A61M 15/004 |
| 9,724,485 B2 * | 8/2017 | Maselli | A61M 16/0048 |
| 2002/0165482 A1 * | 11/2002 | Keldmann | A61M 15/08 604/57 |
| 2006/0217658 A1 * | 9/2006 | Tsutsui | A61M 13/00 604/58 |
| 2007/0125371 A1 | 6/2007 | Djupesland | |
| 2008/0190423 A1 * | 8/2008 | Keldmann | A61M 15/0028 128/203.15 |
| 2010/0114016 A1 | 5/2010 | Gallo et al. | |
| 2010/0242959 A1 * | 9/2010 | Djupesland | A61M 15/0028 128/203.15 |
| 2011/0066136 A1 * | 3/2011 | Moller | A61M 11/08 604/514 |
| 2011/0301572 A1 * | 12/2011 | Vlodaver | A61F 11/00 604/514 |
| 2012/0222678 A1 | 9/2012 | Colbaugh | |
| 2012/0234420 A1 * | 9/2012 | Matsukawa | F16K 15/063 137/538 |
| 2013/0018431 A1 | 1/2013 | Levin | |
| 2013/0298902 A1 * | 11/2013 | Denton | A61M 11/06 128/200.14 |
| 2016/0271352 A1 * | 9/2016 | Chintakis | A61F 5/08 |

FOREIGN PATENT DOCUMENTS

| | | |
|---|---|---|
| JP | 2001-526577 A | 12/2001 |
| JP | 2007-508876 A | 4/2007 |
| JP | 2007-531540 A | 11/2007 |
| WO | 96/22802 A1 | 8/1996 |
| WO | 98/53869 A1 | 12/1998 |
| WO | 02/078774 A1 | 10/2002 |
| WO | 2005/009501 A2 | 2/2005 |
| WO | 2005/037354 A1 | 4/2005 |
| WO | 2015/025324 A1 | 2/2015 |

OTHER PUBLICATIONS

International Search Report and Written Opinion dated Jun. 2, 2017, from International Application No. PCT/US2017/016706.
Notification of Reasons for Refusal dated Dec. 11, 2018, from Japanese Application No. JP 2018-541159, 8 sheets.
Communication pursuant to Rule 164(1) EPC and Supplementary Partial European Search Report completed Aug. 14, 2019, 15 sheets.
Extended European Search Report dated Nov. 27, 2019, from European Application No. 17748346.8, 16 sheets.
Notice of Reasons for Rejection dated Mar. 16, 2021, from Japanese Patent Application No. 2019-119274, 5 sheets.
Notice of Reasons for Rejection dated Mar. 15, 2022, from Japanese Patent Application No. 2019-119274, 2 sheets.

* cited by examiner

MEDICAMENT DELIVERY DEVICE AND METHOD

FIELD OF THE INVENTION

The present invention is directed to a medicament delivery device and method for introducing a medicament into the oral or nasal cavity of a user.

SUMMARY

A medicament delivery device is provided having an oral tubular section for placement in the mouth of a user and a nasal tubular section for placement in the naris of a user. A medicament located in a corrugated, or flexible, section joining the oral tubular section and the nasal tubular section is dispersed into the nasal cavity of the user by blowing into the oral tubular section. A pinch valve or a one way valve is used to prevent the user from accidentally inhaling the medicament. The medicament delivery device may also be used as a pulmonary delivery device into the mouth of a user.

DETAILED DESCRIPTION OF THE INVENTION

Figure 1:
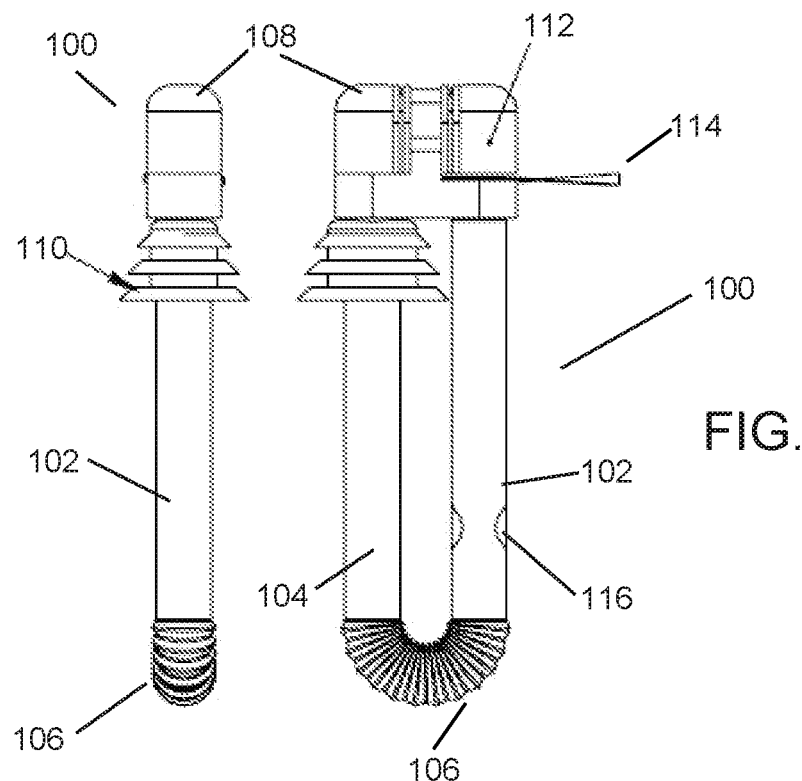
FIG. 1 depicts a side and perspective view of the medicament delivery device.

FIG. 1 depicts a side and a front view of medicament delivery device 100 in a closed position. The medicament delivery device 100 comprises oral tubular section 102, nasal tubular section 104, corrugated section 106, and cover 108. Oral tubular section 102, nasal tubular section 104, and corrugated section 106 are all preferably formed from a pliable, durable plastics such as polypropylene or polyethylene. Corrugated section 106 allows oral tubular section 102 and nasal tubular section 104 to be moved independently of each other. Nasal tubular section 104 further comprises nasal fitting 110 to form a seal with a user's naris as will be described later. Oral tubular section 102 further comprises markings 116 at which a pinch valve is formed.

Cap 108 comprises medicament chamber 112 which contains the medicament to be delivered to the user. In a preferred embodiment, the medicament is in a dry powder form. However, a liquid or any other granular medicament may be employed. A sealing medium 114 retains the medicament in medicament chamber 112 until medicament delivery device 100 is ready to be used by a user. Preferably, the sealing medium 114 resides within a slot in cap 108, with a portion extending from the cap 108 to act as a pull tab, allowing the sealing medium to be removed. The sealing medium slides out along grooves located on the sides of cover 108. In an alternate embodiment, sealing medium 114 may be a food-safe foil seal.

A top portion of oral tubular section 102 resides in cap 108 using a press fit connection and abuts sealing medium 114 in the closed configuration. A top portion of nasal tubular section 104, which extends beyond nasal fitting 110, similarly resides using in cap 108 a press fit connection.

Figure 2:
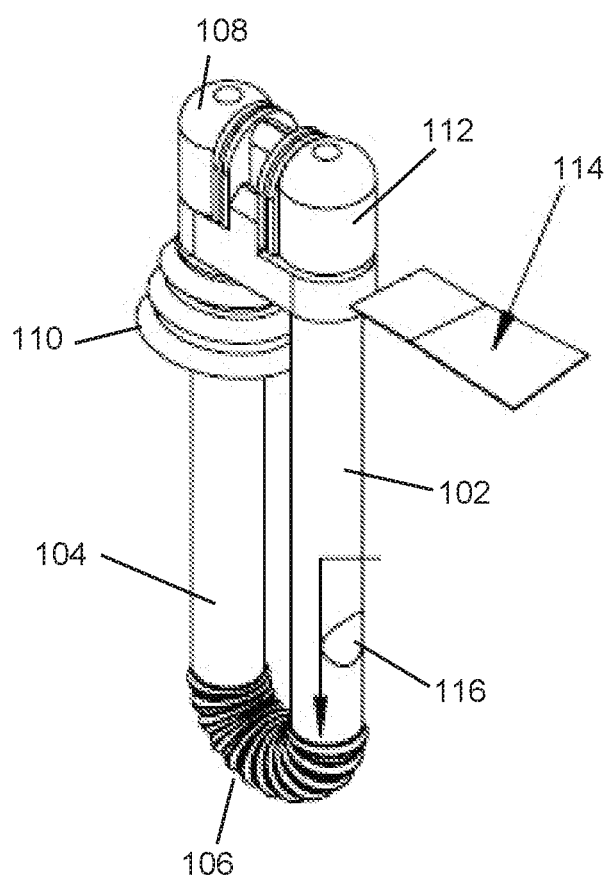
FIG. 2 depicts a perspective view of the medicament delivery device with the sealing medium removed.
Figure 3:
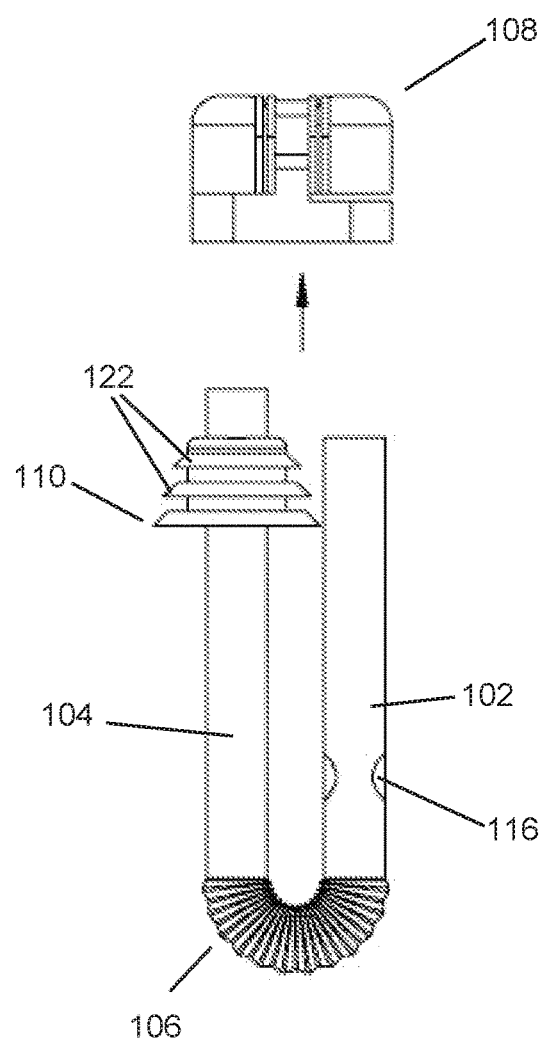
FIG. 3 depicts a side view of the medicament delivery device with the cover removed.

To use medicament delivery device 100, the user first removes sealing medium 114 which causes the medicament contained in medicament chamber 112 to fall into corrugated section 106 through oral tubular section 102 as depicted by the downward arrow in FIG. 2. Next, the user removes cover 108 from medicament delivery device 100 as depicted in FIG. 3. The medicament delivery device 100 is now ready for use by the user.

Figure 4:
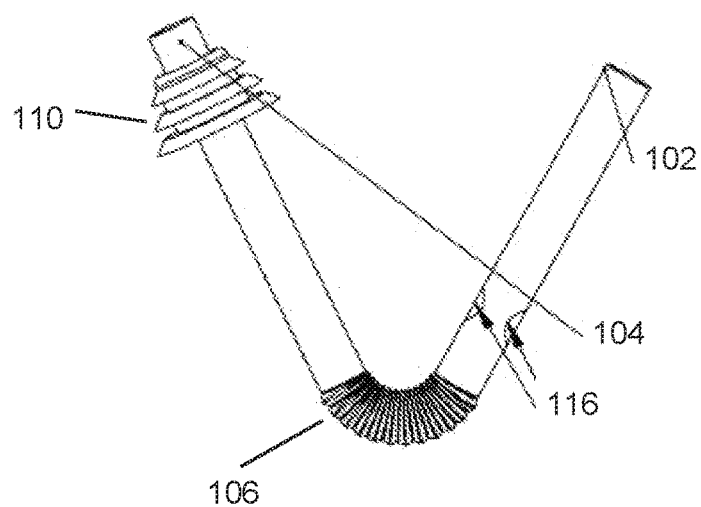
FIG. 4 depicts a side view of the medicament delivery device positioned at an optimal angle.

The user next adjusts oral tubular section 102 and nasal tubular section 104 to an optimal angle as depicted in FIG. 4. As previously described, corrugated section 106 allows oral tubular section 102 and nasal tubular section 104 to be adjusted independently of each other and maintains oral tubular section 102 and nasal tubular section 104 at their adjusted positions. In this embodiment, the user must maintain medicament delivery device in an upright position to prevent the medicament from falling out.

Figure 5:
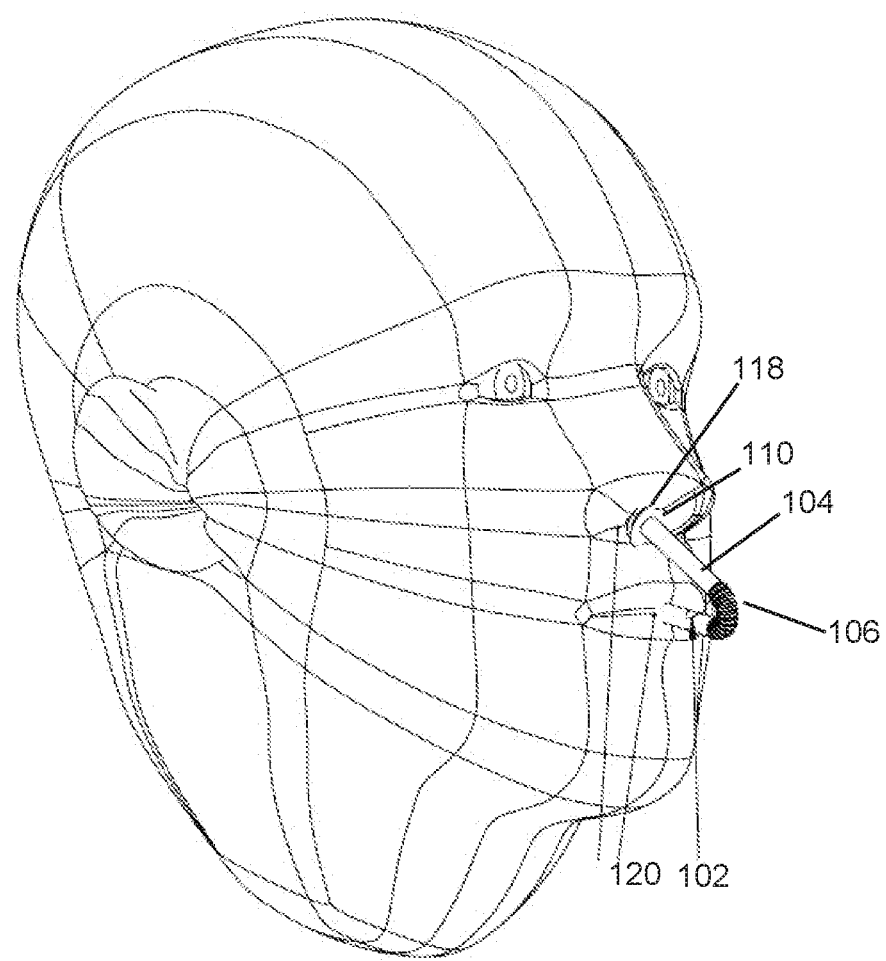
FIG. 5 depicts a view of medicament delivery device placed in the naris and mouth of a user.

The user places nasal tubular section 104 into naris 118 as depicted in FIG. 5. The user also places oral tubular section 102 into mouth 120. During placement of medicament delivery device 100, the user preferably pinches oral tubular section 102 at markings 116 to prevent accidental discharge of the medicament. The sidewalls or oral tubular section 102 may be made of a softer material than the rest of oral tubular section 102, allowing a pinch valve to be formed. Alternatively, the geometry of oral tubular section 102 near markings 116 may be modified to allow a user to easily squeeze the sidewalls together. Any such modifications of oral tubular section 102 which allow for easy deformation may be incorporated into oral tubular section 102. In some embodiments, for ease of manufacture, the markings 116 and the pinch valve may be omitted.

Nasal fitting 110 forms a seal with naris 118 to prevent any leakage. As depicted in FIGS. 3-6, nasal fitting 110 is preferably composed of multi-tiered, pliable rings 122 of increasing diameter. Rings 122 allow a seal to be formed with nares 118 of varying diameters. However, it should be apparent to one of ordinary skill in the art that nasal fitting 110 may be any shape (e.g., conical or without separations between rings 122) as long as it forms a seal with nares 118. For example, nasal fitting 110 may alternatively be cone shaped or flared.

Figure 6:
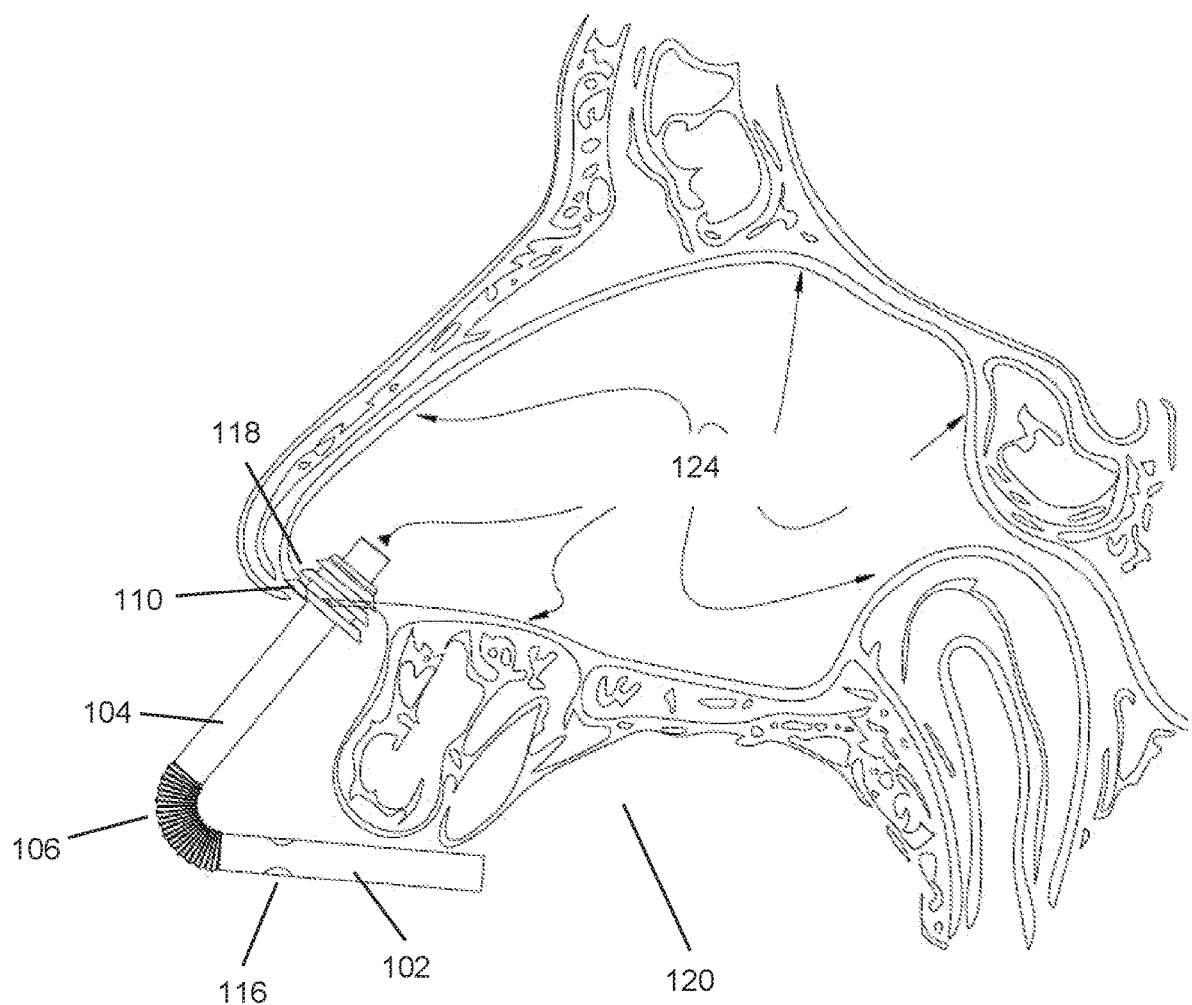
FIG. 6 depicts a side view of the medicament delivery device showing the nasal fitting.

When the user is ready, the user releases oral tubular section 102 at markings 116 and blows into oral tubular section 102. This forces the medicament from corrugated section 106 into nasal cavity 124 as depicted in FIG. 6.

Enhanced dispersion of the medicament is achieved because of the sealing of naris 118 by nasal fitting 110. That is, nasal fitting 110 prevents any leakage of medicament of nares 118 and also ensures that the full force of the air is applied during medicament dispersal, ensuring complete dispersal of the medicament through nasal cavity 124.

Figure 7:
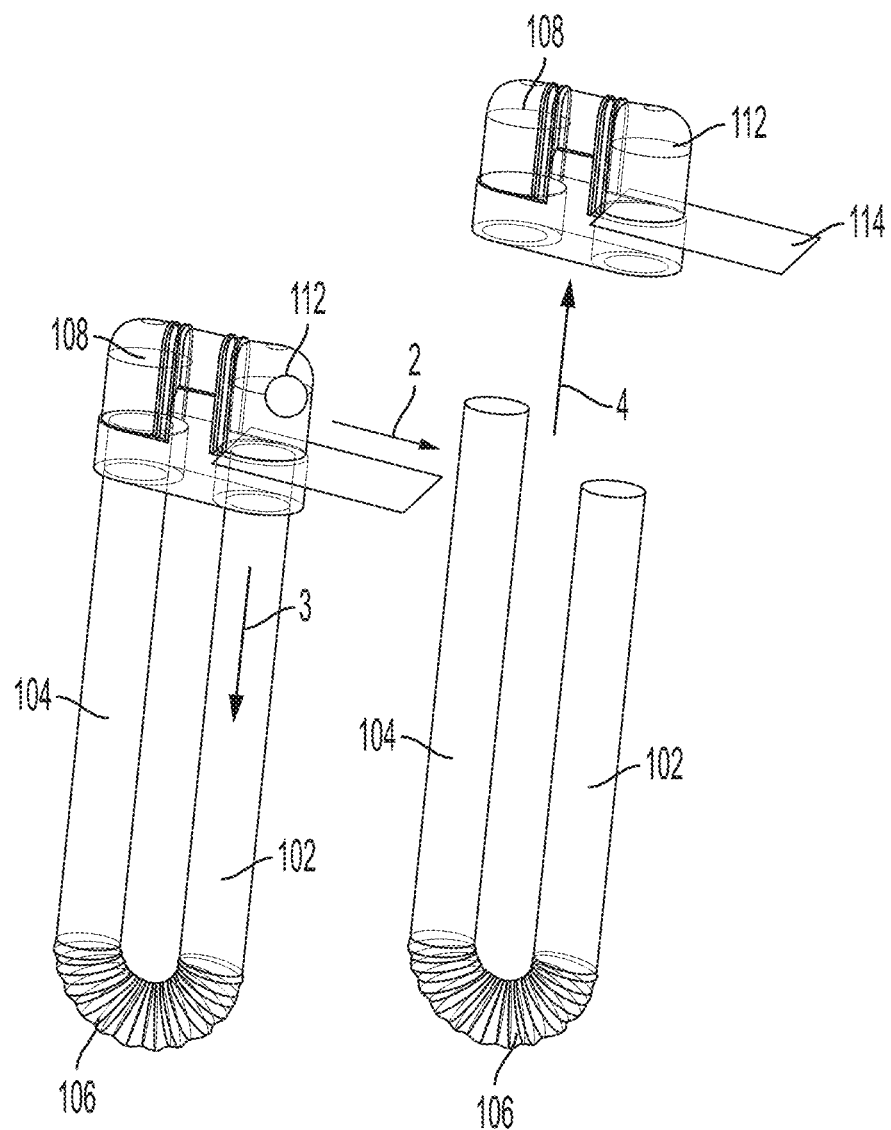
FIG. 7 depicts a view of a pulmonary embodiment of the medicament delivery device.

An alternate pulmonary embodiment of medicament delivery device 100 is depicted in FIG. 7. In this embodiment, the medicament delivery device 100 does not have nasal fitting 110 because the user instead inhales the medicament through oral tubular section 102. The method for using the pulmonary embodiment is substantially similar to that already described with respect to FIGS. 1-7. The user first removes sealing medium 114 (arrow 2) which causes the medicament in medicament chamber 112 to fall into corrugated section 106 (arrow 3). The cap 108 is then removed (arrow 4) and the oral tubular section 102 is placed in the mouth. However, the nasal tubular section 104 here remains open to the environment instead of being placed in nares 118 as shown in FIG. 5.

In this embodiment, either oral tubular section 102 or nasal tubular section 104 may additionally comprise a pinch valve or markings 116 (not shown) to prevent dispersal of the medicament before placement of medicament delivery device 100 in mouth 120.

Figure 8:
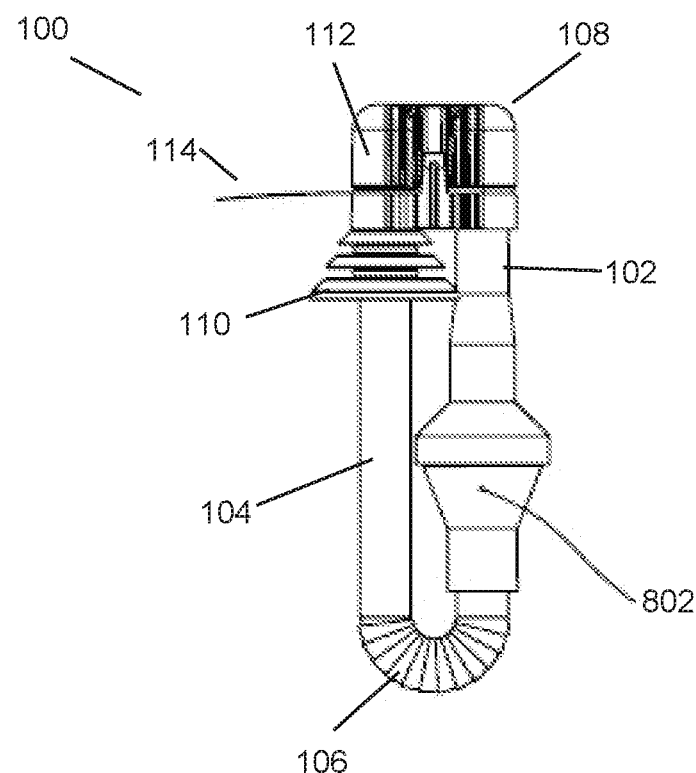
FIG. 8 depicts a view of the medicament delivery device having a one way valve.

Referring next to FIG. 8, depicted is an alternate nasal embodiment of medicament delivery device 100 incorporating a one way valve 802 instead of a manual pinch valve. This embodiment is useful for younger or elderly users that may lack the coordination or ability to use the pinch valve because it prevents accidental inhalation and does not require additional user intervention. The medicament chamber 112 is located in cap 108 above nasal tubular section 104 instead of above oral tubular section 102. Such a change is necessary to ensure that when sealing medium 114 is removed, that the medicament will fall into corrugated section 106. The one way valve 802 would prevent the medicament from entering corrugated section 106 if medicament chamber 112 was located above oral tubular section 102.

Figure 9:
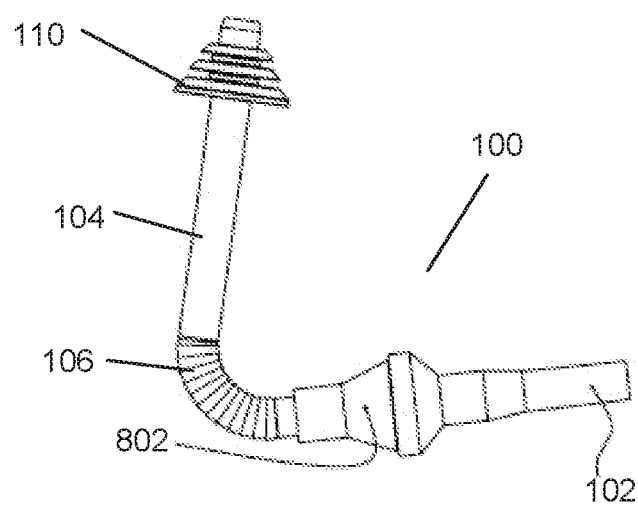
FIG. 9 depicts a view of the medicament delivery device of FIG. 8 with the cover removed.

To use the medicament delivery device of FIG. 8, a user removes sealing medium 114 which causes the medicament to fall into corrugated section 106 through nasal tubular section 104. FIG. 9 depicts medicament delivery device 100 after sealing medium 114 has been removed and cap 108 has been lifted from oral tubular section 102 and nasal tubular section. The medicament delivery device is opened to approximately 80°. The one way valve 802 is oriented such that it only allows airflow from oral tubular section 102 to nasal tubular section 104 and not in the opposite direction. In order to be operated, a minimum cracking pressure must be applied to one way valve 802 through oral tubular section 102.

It is contemplated that many different types of check valves may be used for one way valve 802. Examples of check valves include, but are not limited to diaphragm check valves, swing check valves, stop-check valves, lift-check valves, in-line check valves, duckbill valves, ball valves, butterfly valves, ceramic Disc valves, clapper valves, choke valves, gate valves, globe valves, knife valves, needle valves, piston valves, plug valves, poppet valves, and pneumatic non-return valves. If additional safety is needed to ensure that the user does not inhale the medicament, one way valve 802 may incorporate two or more check valves in series.

Figure 10:
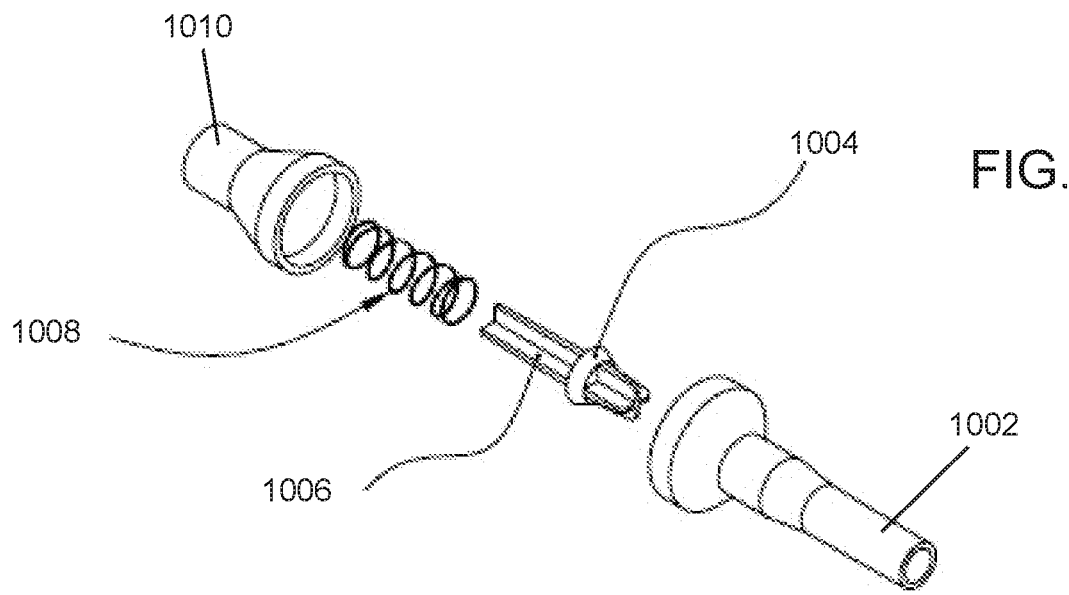
FIGS. 10-13 depicts various views of a one way valve compatible with the medicament delivery device.
Figure 11:
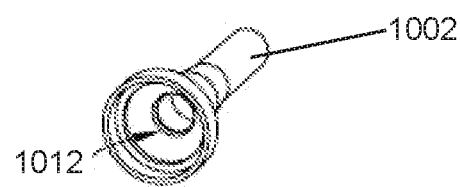

An example of a one way valve 802 compatible with medicament delivery device 100 is depicted in more detail in FIGS. 10-13. As shown in the exploded view of FIG. 10, one way valve 802 generally comprises air inlet section 1002, sealing gasket 1004, shaft 1006, spring 1008, and air outlet section 1010. The one way valve 802 can be incorporated anywhere downstream of the opening of oral tubular section 102 before corrugated section 106. A reversed view of air inlet section 1002 is depicted in FIG. 11. In this view, the tapered valve seal 1012 is visible. The biasing force of spring 1008 (located over shaft 1006) against sealing gasket 1004 against valve seal 1012 prevents any reverse airflow through one way valve 1002. The scaffold construction of shaft 1006 allows the centering of sealing gasket 1004 against valve seal 1012 while minimizing obstruction of airflow once the cracking pressure of one way valve 802 has been reached.

Figure 12:
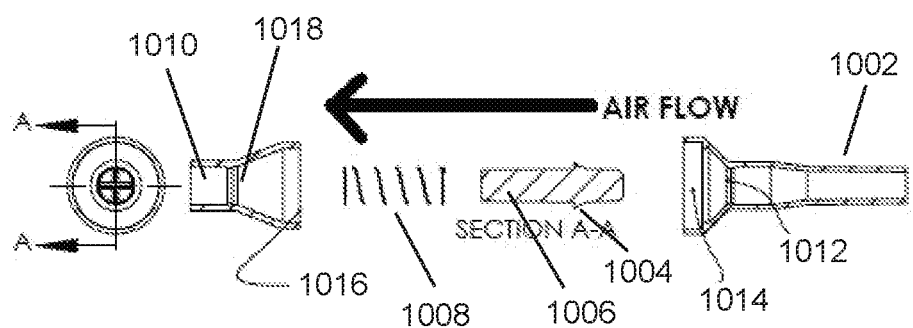
Figure 13:
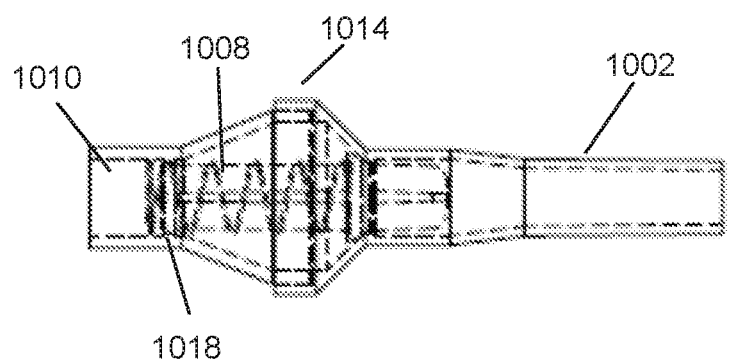

FIG. 13 depicts the components of one way valve 802 fully assembled. As shown in FIGS. 10-12, air inlet section 1002 further comprises locking mechanism 1014 which interlocks with a mating structure 1016 on air outlet section 1010. Preferably, the mating structure allows for a snap fit or threaded connection between air inlet section 1002 and air outlet section 1010. However, an adhesive or other material may also be used to hold the two parts using sonic welding or other mechanical techniques.

One way valve 802 features a widened body to prevent air flow restriction caused by the valve mechanism. For example, if a one way valve were inserted without widening oral tubular section 102, airflow would be restricted which may lead to poor dispersal of the medicament. Outlet section 1010 gradually widens from abutment surface 1018 to mating structure 1016. Similarly, air inlet section gradually widens from valve seal 1012 to locking mechanism 1014

Air outlet section 101 further includes an abutment surface 1018 against which spring 1018 is biased when one way valve 802 is assembled. The opening in the center of abutment surface 1018 is chosen such that it is less than the diameter of spring 1008, but equal to or greater than the diameter of shaft 1006. Thus, when a user blows into air inlet section 1002, for example, spring 1008 compresses and shaft 1006 is free to move in the direction of the airflow. Then, when the airflow is removed, the biasing force of the compressed spring 1008 causes one way valve 802 to reseal (i.e., gasket 1004 contacts valve seal 1012 to prevent reverse airflow).

Figure 14:
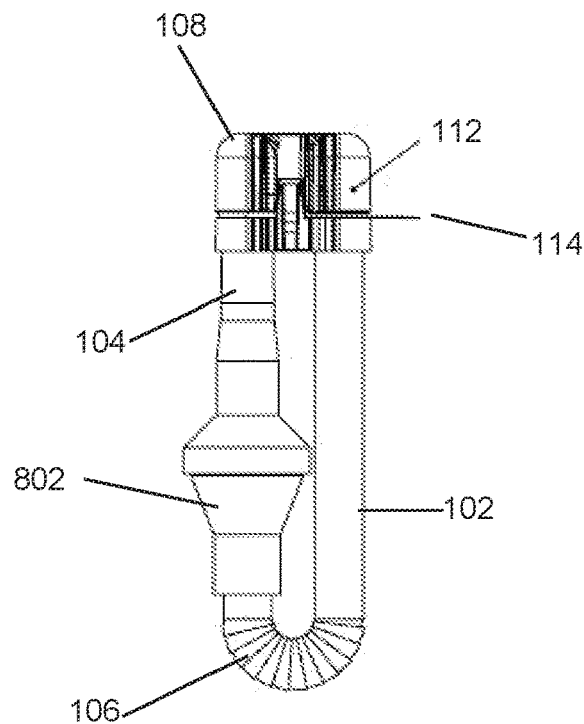
FIGS. 14-15 depict views of a pulmonary embodiment of the medicament delivery device incorporating a one way valve.
Figure 15:
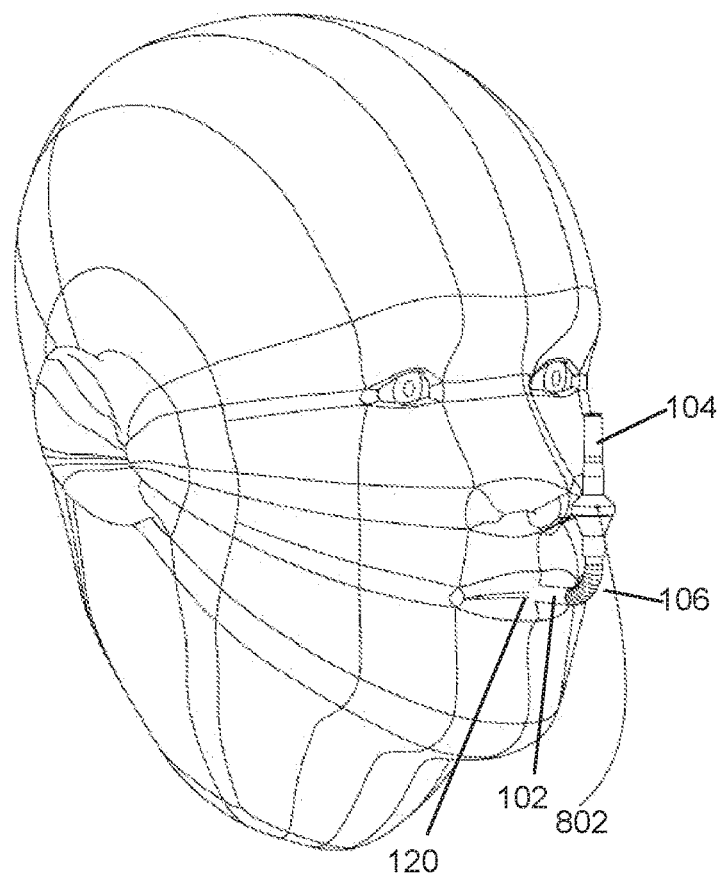

FIGS. 14 and 15 depict a pulmonary version of medicament delivery device 100 incorporating one way valve 802. This embodiment is substantially similar to that already described with respect to FIG. 7, including the operation of the medicament delivery device 100. For clarity and conciseness, only the differences between the medicament delivery device 100 depicted in FIG. 7 and the medicament delivery device 100 depicted in FIGS. 14-15 will be explained. As shown, nasal tubular section 104 here incorporates a one way valve 802 oriented such that air can only be inhaled through oral tubular section 102 and not in the other direction as depicted in FIG. 14. This ensures that the user does not accidentally exhale which would cause the medicament to be ejected through nasal tubular section 104 into the atmosphere. One way valve 802 prevents this from occurring.

Figure 16:
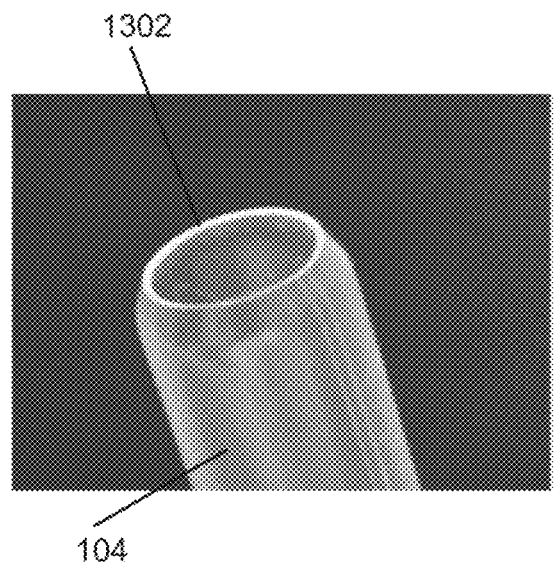
FIGS. 16-17 depict an alternate configuration for the nasal tubular section.
Figure 17:
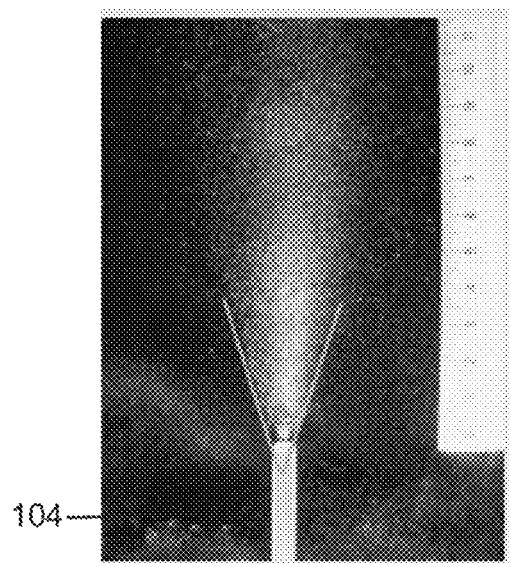

FIGS. 16-17 depict an alternate shape for the proximal end of nasal tubular section 104. As shown, the proximal end of nasal tubular section 104 has a cone-shaped tip 1302 instead of a straight cut as depicted in FIGS. 1-13. Preferably, the cone-shaped tip 1302 has an angle of between 30-40°, more preferably 38°. Cone-shaped tip 1302 causes the medicament to disperse into a plume as shown in FIG.

16. This helps with the delivery of the medicament into naris 118. It should be apparent that other angles for cone-shaped tip 1302 are possible as long as a plume is formed by the medicament.

Figure 18:
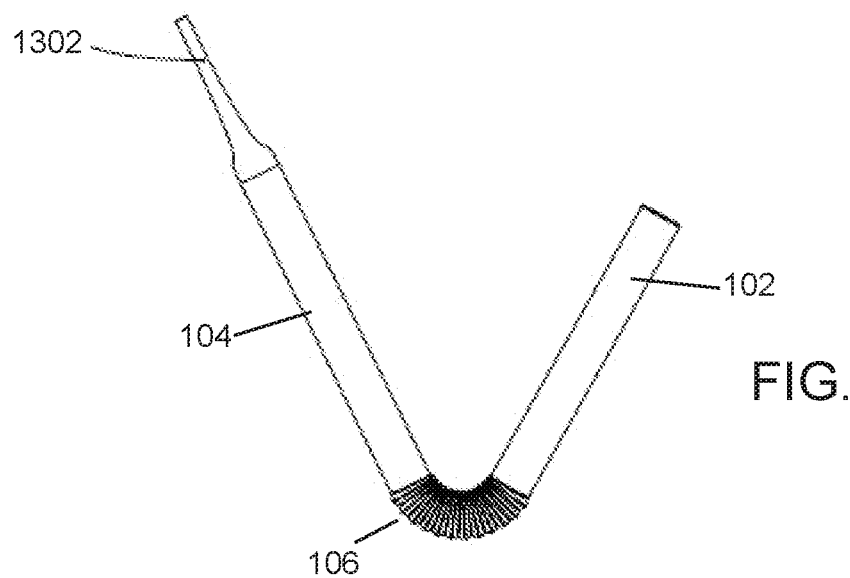
FIG. 18 depicts an alternate tip for the medicament delivery device.

FIG. 18 depicts an alternate shape for cone-shaped tip 1302. Optionally, cone-shaped tip 1302 may be narrowed to provide increased flow (venturi effect) and/or to accommodate users or animals with narrower nasal passages and/or for liquid, as well as powder delivery.

Figure 19:
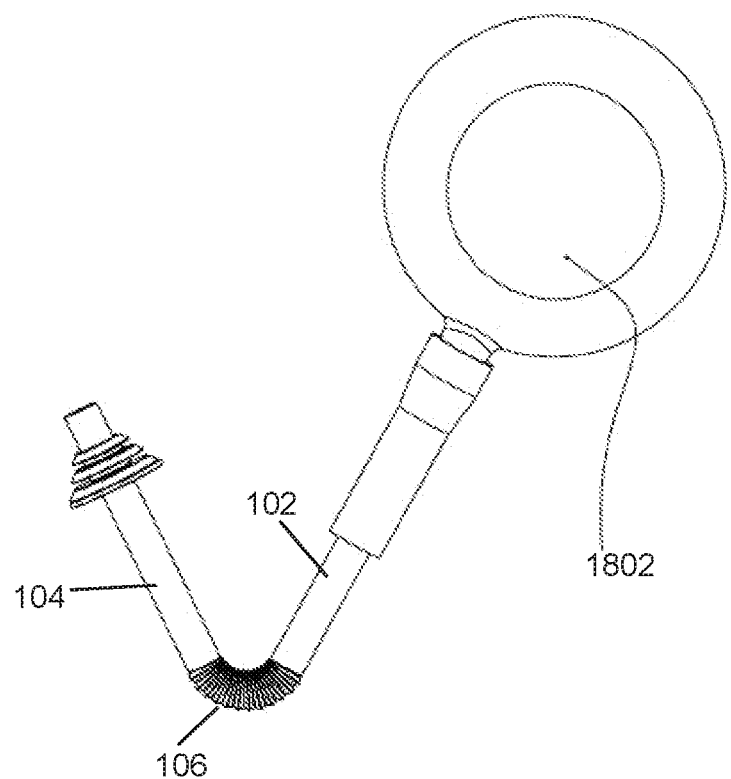
FIG. 19 depicts an alternate embodiment of the medicament delivery device with a squeeze bulb.

FIG. 19 depicts a blowing device 1802 attached to oral tubular section 102. The blowing device 1802 may be a squeeze bulb or other pressure-generating device to accommodate infants, unconscious users, or users and animals otherwise incapable of blowing into the Medicament delivery device 100 with sufficient pressure to deliver the medicament.

The invention claimed is:

1. A medicament delivery device comprising:
a first tubular section;
a second tubular section;
a bendable corrugated section connecting the first tubular section to the second tubular section;
a cap having a medicament chamber holding a medicament and including a sealing member,
a one way valve coupled to an exterior of the second tubular section, wherein the one way valve is configured so as to allow airflow from the second tubular section to the first tubular section and to restrict airflow from the first tubular section to the second tubular section,
wherein the one way valve has a widened body in line with the second tubular section, and the widened body has a greater cross-sectional diameter than second tubular section;
wherein a proximal end of the first tubular section is located within the cap and abuts the sealing member,
wherein the removal of the sealing member causes the medicament to flow through the first tubular section and into corrugations of the bendable corrugated section in a first direction, and
wherein the medicament exits the first tubular section in a second opposite direction during use of the medicament delivery device,
wherein the one way valve comprises:
an air inlet section having a tapered valve seal, an air inlet, and a first mating portion,
wherein the air inlet section is inserted over a first section of the second tubular section;
an air outlet section having an abutment surface, an air outlet, and a second mating portion,
wherein the air outlet is inserted over a second section of the second tubular section,
wherein the first mating portion is jointed to the second mating portion;
a shaft having a first valve stem, a tapered sealing gasket formed circumscribing the shaft, and a second valve stem,
wherein the first valve stem is coupled to a first side of the tapered sealing gasket,
wherein the second valve stem is coupled to a second side of the tapered sealing gasket
wherein the shaft has a proximal end and a distal end, and
wherein the tapered sealing gasket is formed circumscribing the shaft; and
a spring surrounding the first valve stem,
wherein a proximal end of the spring is configured so as to abut the abutment surface and a distal end of the spring is configured so as to exert a biasing force against the tapered sealing gasket, causing the tapered sealing gasket to form an airtight connection with the tapered valve seal to restrict airflow from the air outlet section to the air inlet section,
wherein the first valve stem has a cross-bar shape,
wherein the second valve stem has the cross-bar shape, and
wherein the cross-bar shape is an X-shape.

2. The medicament delivery device according to claim 1, further comprising:
a second one way valve located in series with the one way valve along the interior of the second tubular section wherein the one way valve is located.

3. The medicament delivery device according to claim 1, wherein, when the air inlet receives an airflow force greater than the biasing force of the spring, the spring is compressed and the airtight connection is removed, allowing airflow from the air inlet to the air outlet.

4. The medicament delivery device according to claim 1, further comprising:
a nasal fitting located on the first tubular section;
wherein the nasal fitting is configures so as to form an airtight seal with the naris of a user when the nasal fitting is inserted into the naris, and
wherein the nasal fitting comprises a plurality of multi-tiered pliable rings of increasing diameter.

5. The medicament delivery device according to claim 4, wherein the nasal fitting is without separations between the rings.

6. The medicament delivery device according to claim 5, further comprising:
a cone-shaped tip located at the proximal end of the first tubular section, and
wherein the cone-shaped tip extends beyond the nasal fitting such that the cone-shaped tip is located completely within a nasal cavity of the user when the nasal fitting is inserted into the naris of the user.

7. The medicament delivery device according to claim 6, wherein sides of the proximal end of the first tubular section are angled inwards at 30-40° to form the cone-shaped tip.

8. The medicament delivery device according to claim 7, wherein the sides of the proximal end of the first tubular section are angled inwards at 38°.

9. The medicament delivery device according to claim 1, wherein the first valve stem is longer than the second valve stem.

* * * * *